United States Patent [19]

Martel et al.

[11] 4,128,584
[45] Dec. 5, 1978

[54] OPTICALLY ACTIVE SULFONATES OF ALLETHROLONE

[75] Inventors: Jacques Martel, Bondy; Jean Tessier, Vincennes, both of France

[73] Assignee: Roussel Uclaf, Paris, France

[21] Appl. No.: 807,069

[22] Filed: Jun. 16, 1977

[30] Foreign Application Priority Data

Jun. 23, 1976 [FR] France .................. 76 19087

[51] Int. Cl.² .................. C07C 45/24; C07C 45/00
[52] U.S. Cl. .................. 260/586 R; 260/456 R
[58] Field of Search .................. 260/456 R, 586 R

[56] References Cited

U.S. PATENT DOCUMENTS

| 2,891,888 | 6/1959 | Guest et al. | 260/586 R |
| 3,720,703 | 3/1973 | Elliot et al. | 260/586 R |
| 4,005,146 | 1/1977 | Goffinet | 260/586 R |

OTHER PUBLICATIONS

La Forge et al., "J. Org. Chem.," 19, 457(1954).

La Forge et al., "J.A.C.S.," 74(1952), 5392.

*Primary Examiner*—Norman Morgenstern
*Attorney, Agent, or Firm*—Hammond & Littell

[57] ABSTRACT

Optically active sulfonates of allethrolone of the formula

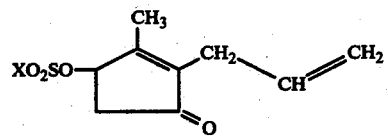

wherein X is selected from the group consisting of alkyl of 1 to 3 carbon atoms and phenyl optionally substituted in the para position with a member selected from the group consisting of methyl, fluorine, chlorine and bromine with an (R) or (S) configuration which are useful for obtaining optically active allethrolone of antipodal configuration and process for their preparation.

4 Claims, No Drawings

OPTICALLY ACTIVE SULFONATES OF ALLETHROLONE

OBJECTS OF THE INVENTION

It is an object of the invention to provide the novel sulfonates of allethrolone of formula I and to provide a novel process for their preparation.

It is another object of the invention to provide a novel process for obtaining optically active allethrolone of antipodal configuration.

These and other objects and advantages of the invention will become obvious from the following detailed description.

THE INVENTION

The novel compounds of the invention are optically active sulfonates of allethrolone of the formula

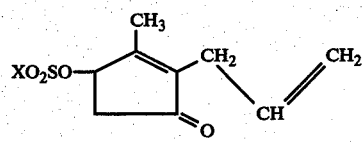

wherein X is selected from the group consisting of alkyl of 1 to 3 carbon atoms and phenyl optionally substituted in the para position with a member selected from the group consisting of methyl, fluorine, chlorine and bromine with an (R) or (S) configuration.

Among the preferred compounds of the invention are methane sulfonate of allethrolone of (R) configuration, methane sulfonate of allethrolone of (S) configuration, ethane sulfonate of allethrolone of (R) configuration, ethane sulfonate of allethrolone of (S) configuration, p-toluene sulfonate of allethrolone of (R) configuration, p-toluene sulfonate of allethrolone of (S) configuration, p-chlorobenzene sulfonate of allethrolone of (R) configuration, p-chlorobenzene sulfonate of allethrolone of (S) configuration, p-bromobenzene sulfonate of allethrolone of (R) configuration and p-bromobenzene sulfonate of allethrolone of (S) configuration.

The novel process of the invention of the preparation of the sulfonates of formula I comprises reacting optically active allethrolone of (R) or (S) configuration with a sulfonyl chloride of the formula

where X has the above definition in at least one organic solvent in the presence of a basic agent. The said basic agent is preferably a tertiary base, most preferably triethylamine. Generally, the reaction temperature is preferably $-15°$ to $0°$ C.

The organic solvent is preferably selected from the group consisting of aliphatic ketones of 3 to 6 carbon atoms, monocyclic aromatic hydrocarbons, ether oxides and chlorinated solvents and mixtures thereof. Examples of specific solvents are acetone, methylethylketone, methylisobutylketone, benzene, toluene, xylene, ethyl ether, isopropyl ether, tetrahydrofuran, methylene chloride, dichloroethane, carbon tetrachloride and mixtures thereof. Preferably, the solvent is acetone or toluene.

The preferred sulfonic acid chloride for condensation with optically active allethrolone is methane sulfonyl chloride and the condensation is preferably effected in acetone or toluene in the presence of triethylamine at a preferred temperature of $-15°$ to $30°$ C. The process may also preferably be effected with p-toluene sulfonyl chloride in the presence of methylene chloride or tetrahydrofuran in the presence of triethylamine at a preferred temperature of $-30°$ to $0°$ C.

The sulfonates of formula I, particularly the methane sulfonates and p-toluene sulfonates of optically active allethrolone, are useful for obtaining allethrolone of configuration antipodal to that possessed by the allethrolone used to prepare the sulfonates and the sulfonates themselves. In effect, the hydrolysis of the sulfonates of formula I in a basic media results in the reversal of asymmetrical center of allethrolone and permits the obtention of optically active allethrolone with a configuration antipodal to that of the starting sulfonate.

The process of the invention for the preparation of optically active allethrolone comprises subjecting an optically active sulfonate of formula I to hydrolysis in a basic media to obtain optically active allethrolone with a configuration opposite to that possessed by the suflonate.

The hydrolysis is preferably effected with a basic agent selected from the group consisting of ion exchange resins of a basic character, alkali metal carbonates and bicarbonates and alkali metal hydroxides with the latter being used at most in substantially stoichiometric quantities. The preferred basic agents are alkali metal carbonates or bicarbonates. The hydrolysis is preferably effected in an organic solvent which is not water-miscible and is preferably methylene chloride or dichloroethane.

The hydrolysis conditions are particularly important to obtain a satisfactory yield of the inverse allethrolone. The basic agent used should be sufficiently strong to permit the obtention of the alcohol from the ester of allethrolone and in practice, the alkali metal carbonates and bicarbonates permit the transformation under satisfactory conditions when the reaction is effected in a non-water-miscible organic solvent which dissolve allethrolone as it is formed and diminishes the possibility of alteration of the alcohol. Strong bases such as sodium hydroxide or potassium hydroxide, for example, are equally useful under the condition that an excess greater than the theoretical amount is not used.

The use of the sulfonates of optically active allethrolone of formula I to obtain optically active allethrolone of inverse configuration to that of the starting sulfonate is of great industrial importance. It is known that, in general, optically active allethrolone of (S) configuration leads by esterification with cyclopropane carboxylic acids to esters with clearly greater insecticidal activity than the esters of the same acids with racemic allethrolone or allethrolone of (R) configuration. To prepare (S) allethrolone, one usually uses a resolution process such as described in French Pat. No. 2,166,503 which after recovery of the desired (S) allethrolone leaves (R) allethrolone.

It is evident that it would be very advantageous to be able to convert the optically active (R) allethrolone into the optically active (S) allethrolone since the esters of the latter possess the greater insecticidal activity. This important industrial problem has been studied and the first proposed solution is described in copending, commonly assigned U.S. Pat. application Ser. No. 795,021 filed May 9, 1977 wherein the racemization described represents an important advance over the prior art. However, the said process still requires resolution of racemic allethrolone to obtain optically active (S) allethrolone and finally relatively complex operations that have to be resumed.

Continuing studies of the problems of this field were made and give to the problem of recovering optically active (R) allethrolone a more advantageous solution than that which consists of intermediate racemization of allethrolone. The process allows the direct conversion of optically active (R) allethrolone into optically active (S) allethrolone in only 2 steps and under conditions easily attainable industrially.

The preferred process of the invention comprises hydrolyzing a sulfonate of allethrolone of formula I with a (R) configuration and is preferably effected with an aqueous solution of potassium carbonate in the presence of methylene chloride or dichloroethane to obtain optically active (S) allethrolone.

When optically active (S) allethrolone is obtained by resolution of racemic allethrolone, the residue remaining is generally a mixture of (R) and (S) allethrolone with (R) allethrolone being the major constituent. These mixtures can be transformed into mixtures of sulfonates of optically active allethrolone rich in the sulfonate of (R) allethrolone and then into allethrolone of (S) configuration by the process of the invention which is also an object of the invention. The preferred sulfonate is the methane sulfonate.

The process of the invention for the preparation of sulfonates of optically active allethrolone as well as the process of inversion of allethrolone by hydrolysis in a basic media of the said sulfonates have an unexpected character. Allethrolone presents, in effect, a very special structure of cyclic allylic alcohol which has 2,3-double bond in the ring which activates the alcoholic hydroxyl and a ketone group which activates the hydrogen α to the alcohol function. While at first place it might appear easy, the preparation of sulfonates of allethrolone has serious difficulties because of the special reactivity of the alcohol.

The preparation of a sulfonate of allethrolone by reaction of allethrolone with a sulfonyl chloride in the presence of a basic agent is accompanied by formation of the chloride or hydrochloride of the base used. For the esterification to be sufficiently complete, it is practical to use an excess of the sulfonyl chloride and the base with respect to the allethrolone used in the reaction.

The methane sulfonate of allethrolone formed can then react notably with the hydrochloride of the base and form a chlorinated derivative of the formula

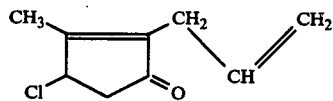

A with the asymetric carbon inverse to the starting material. The said chloride or its sulfonic acid ester precursor in the presence of an excess of base can also lead to a diene of the formula

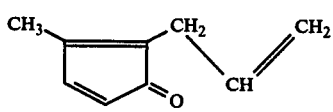

B which by the Diels-Alder reaction can form dimers of the formulae

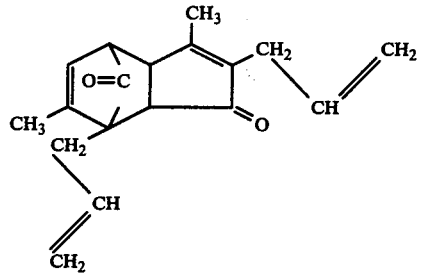

C and

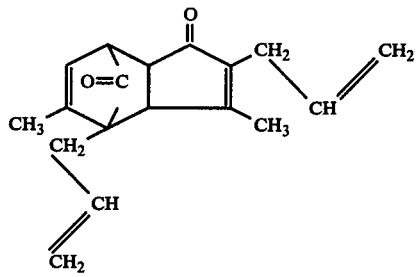

The choice of tertiary bases, preferably triethylamine, use of solvents in which the chloride or hydrochloride of the base used are only slightly soluble as well as use of a reaction temperature not too high permits the avoidance of the undesired side reactions under the preferred conditions of the process of the invention.

However, there was fear especially that hydrolysis of sulfonates of allethrolone in a basic media in the course of which, according to the process, object of the invention, the inversion of allethrolone is effected would give secondary reactions of the type described by La Forge [J.A.C.S., Vol. 74 (1952), p. 5392] which lead to formation of dimers analogous to compounds of formula C discussed above. However, the process of the invention for hydrolysing the sulfonates avoids the undesired side reactions, particularly in the preferred modes of the process, by utilizing relatively weak bases or strong bases used in a quantity at most equal to the stoichiometric quantity as well as by the use of a solvent which is not miscible with water. The process permits the practical realization of the inversion of the asymmetric center of allethrolone in an unexpected manner with interesting yields in spite of the difficulties due to the particular structure of the alcohol which difficulties would, a priori, under the practical success of such a process not very probable.

In the following examples there are described several preferred embodiments to illustrate the invention. However, it should be understood that the invention is not intended to be limited to the specific embodiments.

EXAMPLE 1 methane sulfonate of (R) allethrolone

A mixture of 50 g of (R) allethrolone [determined by circular dischroism to be 92% (R) isomer and 8% (S) isomer] in 100 ml of acetone was cooled to −15° C and 61 ml of triethylamine were added thereto. A solution of 43 g of methane sulfonyl chloride in 33 ml of acetone was slowly added thereto and the mixture was stirred for 30 minutes at −10° C and was then poured into a mixture of 165 ml of aqueous N hydrochloric acid and 330 ml of water. The mixture was stirred and 660 ml of methylene chloride were added thereto. After stirring, the organic phase was decanted. The aqueous phase was extracted with another 660 ml of methylene chloride and the combined organic phases were dried and evaporated to dryness to obtain 79.8 g of methane sulfonate of (R) allethrolone.

RMN Spectrum (deuterochloroform)

Peak at 128 Hz characteristic of hydrogens on 3-methyl of allethrolone; peaks at 160 to 190 Hz characteristic of hydrogens at 5-position of allethrolone and hydrogen in allylic chain of allethrolone; peak at 187 Hz characteristic of hydrogens of methyl of the sulfonate; peaks at 295 and 345 Hz characteristic of hydrogens of terminal carbon of allylic chain of allethrolone peaks at 320 to 345 Hz characteristic of hydrogens of 4-position of allethrolone and 2'-hydrogen of allylic chain.

EXAMPLE 2

46 ml of triethylamine were added at −6° C to a solution of 36.2 g of (R) allethrolone in 400 ml of a 1—1 benzene-ether mixture and a solution of 20 ml of methane sulfonyl chloride in 270 ml of a 1—1 benzene ether mixture was slowly added thereto. The mixture was stirred for 3 hours at −10° C and was then poured into a dilute solution of hydrochloric acid. The organic phase was decanted and the aqueous phase was extracted with ether. The combined organic phases were washed with water, dried and evaporated to dryness under reduced pressure to obtain 53 g of methane sulfonate of (R) allethrolone with the same characteristics as the product of Example 1.

EXAMPLE 3

225 g of methane sulfonyl chloride were added over 10 minutes at −13° C to a solution of 250 g of (R) allethrolone with a specific rotation $[\alpha]_D = -10.5°$ (c = 10% in chloroform) in 750 ml of toluene and a solution of 217.5 g of triethylamine in 200 ml of toluene was added thereto over 2 hours at −8° C. The mixture was stirred for 10 minutes and then 1000ml of water were added at −5° C over 30 minutes. The mixture was stirred and the organic phase was decanted. The aqueous phase was extracted with toluene and the combined organic phases were washed with water. The wash water was extracted with toluene and the combined toluene phases were dried and evaporated to dryness under reduced pressure to obtain 370 g of methane sulfonate of (R) allethrolone having the same characteristics of the product of Example 1.

EXAMPLE 4 p-toluene sulfonate of (R) allethrolone

First, 8.6 g of (R) allethrolone and then 16 ml of triethylamine were added at −40° C to 50 ml of methylene chloride and a solution of 21.4 g of p-toluene sulfonyl chloride in 150 ml of methylene chloride was added thereto over 15 minutes at −40° C. The mixture was stirred for 48 hours at −17° C and was then poured into an aqueous iced 0.1N hydrochloric acid solution. The mixture was stirred and the aqueous phase was extracted with ether. The ether extracts were washed with water and dried over magnesium sulfate to obtain 18.5 g of raw product. The latter was chromatographed over silica gel and was eluted with a 9-1 benzene-ethyl acetate mixture to obtain 3.7 g of p-toluene sulfonate of (R) allethrolone.

I.R. Spectrum (chloroform)

absorption at 1718 cm$^{-1}$ (carbonyl); complex absorption at 1662, 1657 and 1646 cm$^{-1}$ (double bond of allethrolone ring); absorptions at 1605 and 1498 cm$^{-1}$ (aromatic ring); absorption at 990 and 920 cm$^{-1}$ (allylic double bond of allethrolone); and absorptions at 1375, 1192 and 1180 cm$^{-1}$ (—SO$_2$).

RMN Spectrum (deuterochloroform)

Peak at 119 Hz characteristic of hydrogens of 3-methyl of allethrolone; peaks at 142.5-152.5 Hz characteristic of 5-hydrogen of allethrolone; peak at 146.5 Hz characteristic of hydrogens of methyl of p-tolyl; peaks at 173.5-179.5 Hz characteristic of hydrogen in 1-position of allylic chain of allethrolone; peaks at 290°-305 Hz characteristic of terminal hydrogens of allylic chain of allethrolone; peaks at 315 to 360 Hz characteristic of hydrogen in 2'-position of allylic chain of allethrolone; peaks at 315 to 360 Hz characteristic of hydrogen in 4-position of allethrolone ring; and peaks at 437, 446, 466 and 474 Hz characteristic of aromatic protons.

EXAMPLE 5

(S) allethrolone from methane sulfonate of (R) allethrolone

A solution of 79.8 g of the methane sulfonate of (R) allethrolone of Example 1 in 500 ml of methylene chloride was added to a solution of 50 g of potassium carbonate in 500 ml of water and the mixture was refluxed with stirring for 42 hours. The methylene chloride was distilled and the residual aqueous phase was extracted with heptane. The aqueous phase was saturated with sodium chloride, stirred and extracted with methylene chloride. The organic extracts were dried and evaporated to dryness and the residue was rectified under reduced pressure to obtain 33.4 g of (S) allethrolone with a boiling point of 92° C at 0.2 mm Hg and a specific rotation $[\alpha]_D^{20} = 11.5° \pm 1°$ (c = 1.5% in chloroform).

| U.V. Spectrum (ethanol): | | |
|---|---|---|
| Max. at 231 nm | $E_1^1 = 807$ | $\epsilon = 12,300$ |
| Max. at 306 nm | $E_1^1 = 4$ | |
| Circular Dichroism (dioxane): | | |
| Inflex. towards 345 nm | $\Delta\epsilon = +1.14$ | |
| Max. at 332 nm | $\Delta\epsilon = +2.32$ | |
| Max. at 320 nm | $\Delta\epsilon = +2.53$ | |
| Inflex. towards 310 nm | $\Delta\epsilon = +1.91$ | |
| Max. at 230 nm | $\Delta\epsilon = -15.6$ | |

From the circular dichroism, it is ascertained that the allethrolone product was 88% of the (S) isomer and 12% of the (R) isomer.

Various modifications of the process or products of the invention may be made without departing from the spirit or scope thereof and it is to be understood that the invention is intended to be limited only as defined in the appended claims.

We claim:

1. A process for the preparation of optically active allethrolone comprising subjecting an optically active sulfonate of the formula

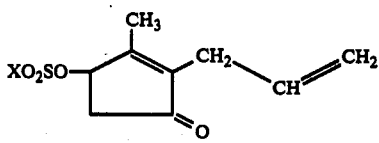

wherein X is selected from the group consisting of alkyl of 1 to 3 carbon atoms and phenyl optionally substituted in the para position with a member selected from the group consisting of methyl, fluorine, chlorine and bromine with an (R) or (S) configuration to hydrolysis with a base selected from the group consisting of ion exchange resins of a basic nature, alkali metal carbonates and bicarbonates and alkali metal hydroxides with the latter being used at most in stoichiometric amounts in a water-immiscible organic solvent to obtain optically active allethrolone with a configuration opposite to that possessed by the sulfonate.

2. The process of claim 1 wherein the sulfonate is that of (R) allethrolone.

3. The process of claim 1 wherein the sulfonate is a mixture of sulfonates of (R) allethrolone and (S) allethrolone with the (R) isomer being the major component.

4. The process of claim 1 wherein the sulfonate is the methane sulfonate.